United States Patent [19]

Bergeron et al.

[11] 4,247,490

[45] Jan. 27, 1981

[54] PROCESS FOR THE PURIFICATION OF DIALKYLPHOSPHOROCHLORIDOTHIOATES

[75] Inventors: Charles R. Bergeron, Baton Rouge; Alfred P. Anderson, Gonzales; Thomas J. Walter, Baton Rouge, all of La.

[73] Assignee: Ethyl Corporation, Richmond, Va.

[21] Appl. No.: 73,684

[22] Filed: Sep. 10, 1979

[51] Int. Cl.$^3$ .............................................. C07F 9/20
[52] U.S. Cl. .................................................... 260/990
[58] Field of Search ........................................ 260/990

[56] References Cited

U.S. PATENT DOCUMENTS

| 3,356,774 | 12/1967 | Niermann et al. | 260/981 |
| 3,836,610 | 9/1974 | Diveley | 260/986 |
| 3,897,523 | 7/1975 | Sorstokke | 260/986 |
| 4,025,586 | 5/1977 | Lippman | 260/986 |
| 4,075,992 | 2/1978 | Vopel et al. | 260/986 |
| 4,159,289 | 6/1979 | Anderson et al. | 260/990 |

*Primary Examiner*—Anton H. Sutto
*Attorney, Agent, or Firm*—Donald L. Johnson; John F. Sieberth; James M. Pelton

[57] ABSTRACT

A process for purification of dialkyl phosphorochloridothioate by contacting a crude material containing oxygenated phosphorus compound impurities with an alcohol and separating the product dialkyl phosphorochloridothioate from the reaction product, for example, by distillation.

18 Claims, No Drawings

PROCESS FOR THE PURIFICATION OF DIALKYLPHOSPHOROCHLORIDOTHIOATES

BACKGROUND OF THE INVENTION

This invention relates to a process for treatment and separation of O,O-di-($C_{1-8}$-alkyl)-phosphorochloridothioates from a mixture thereof with certain impurities. The O,O-dialkyl-phosphorochloridothioates are valuable intermediates, for instance, in the preparation of lubricant additives and insecticides. Particularly, O,O-diethyl thiophosphoryl chloride is an intermediate in the synthesis of an insecticide known generically as parathion and O,O-dimethyl thiophosphoryl chloride is an intermediate for the synthesis of an insecticide generically called methyl parathion. Such are also useful in the manufacture of diazinon, chlorpyrifus, fensulfothion and the like.

Several methods have been taught in the patent literature for the synthesis of the esters of phosphorochloridothioic acid including one-step and two-step methods. In the one-step process, phosphorus pentasulfide, alcohol and chlorine are reacted to prepare the ester corresponding to the alcohol and then the solvent is removed and the product separated.

In the two-step process, the first process step reacts phosphorus pentasulfide with an alcohol, such as ethanol, so as to form O,O-diethyl dithiophosphoric acid and hydrogen sulfide, and in a second process step the isolated O,O-diethyl dithiophosphoric acid is chlorinated in an appropriate solvent with chlorine gas, resulting in the formation of O,O-diethyl thiophosphoric acid chloride. Conventionally, the alkyl groups in the dialkyl phosphorochloridothioates have from 1 to 8 carbon atoms and are generally selected from methyl, ethyl, isopropyl, butyl, sec.-butyl, t-butyl, and the like, up through n-octyl and isomers thereof. However, each of these conventional one-step and two-step processes produces impurities such as phosphates which must be separated from the product. Several solutions to the impurity problem have been proposed in the prior art. In one process, the product is simply distilled under reduced pressure from the reaction vessel. The sump temperature increases to about 150° C. during distillation, and upon cooling after terminating distillation the liquid sump phase solidifies and consists essentially of elementary sulfur (confer U.S. Pat. No. 3,356,774). However, some impurities have such close boiling points that they cannot be separated as produced from the desired O,O-dialkyl phosphorochloridothioate product.

In another prior art patent disclosing a one-step process, the reaction mixture is treated with hydrogen sulfide to convert the sulfur monochloride formed during the reaction of chlorine with the dialkyl dithiophosphoric acid. When the hydrogen sulfide treatment is carried out at relatively low temperature, a precipitate of sulfur is obtained with practically no by-products. Then, by distilling under vacuum and washing the distillate with water, the diesters of phosphorochloridothioic acid are obtained in very high yield and very high degree of purity (U.S. Pat. No. 3,502,750). Unfortunately, such water washing processes require extensive capital investment for equipment and take additional product losses from hydrolysis. In another prior art process using a two-stage chlorination reaction technique, the reaction mixture is chlorinated and then established and maintained at a temperature in the range of 85°–110° C. until it is substantially free of sulfur monochloride and the relatively thermal unstable sulfur that forms becomes more thermally stable so that the product dialkyl thiophosphoryl chloride can be readily and safely removed from the mixture thereof with sulfur by distillation (U.S. Pat. No. 3,836,610).

Further, U.S. Pat. No. 3,897,523 teaches a purification process in which the crude dialkyl phosphorochloridothioate is vaporized in a film evaporator, the vapor is condensed, washed with water at 10° to 60° C., the organic and aqueous phases are separated and the organic phase is vacuum dried. In U.S. Pat. No. 4,025,586, the product dialkyl phosphorochloridothioate is distilled and the distillation residue is water washed to hydrolyze impurities and the washed residue is dried and recycled to the chlorination step.

However, all of the prior art distillation processes do not effect removal of dialkyl phosphates which have similar boiling points to the product dialkyl phosphorochloridothioates of this invention. Known processes which do effect removal of dialkyl phosphates require extensive water washing with increased equipment and its associated capital and operating costs and with additional product losses.

Not only are oxygenated phosphorus impurities, such as alkyl dichlorophosphates and dialkyl chlorophosphates, produced during the reaction as by-products, but the desired dialkyl phosphorochloridothioates may be thermally degraded over time in purification equipment to produce additional by-products of the same sort. The thermal degradation of diethyl phosphorochloridothioate is illustrative of what may occur during processing operations. A sample of diethyl phosphorochloridothioate was found to contain 88.4 area percent diethyl phosphorochloridothioate and 0.48 area percent diethyl chlorophosphate by vapor phase chromatography. The sample was split in two parts and one was purged with air while the other was purged with nitrogen. The samples were heated at 140° C. for 3 hours. Samples taken after one-half hour and 3 hours were analyzed with the results shown below:

| Increase of Oxygenated Phosphorus Impurities With Time at 140° C. | | | |
|---|---|---|---|
| Time, Hrs. | 0 | ½ | 3 |
| Air Purge | | | |
| Diethylphosphorochloridothioate (Area %) | 88.4 | 87.3 | 78.9 |
| Diethylchlorophosphate (Area %) | 0.48 | 0.59 | 2.4 |
| $N_2$ Purge | | | |
| Diethylphosphorochloridothioate (Area %) | 88.4 | 87.1 | 71.4 |
| Diethylchlorophosphate (Area %) | 0.48 | 0.68 | 2.3 |

From the above data, it is clear that the impurity has increased fivefold while there was a 9–20% decrease in desired product. Such high impurity levels are undesirable because the end-product insecticides have been registered with governmental agencies as having been tested and found safe and effective with certain impurities at not greater than certain concentrations. Therefore, it is critical to maintain impurity identities and levels at or below those allowed in governmental registrations and as stated on label certifications for the end product.

Without limiting the invention in any manner and without advocating any particular mechanism or theory of action, it is believed that degradation of dialkyl phosphorochloridothioates could possibly take place according to the following chemical reaction scheme:

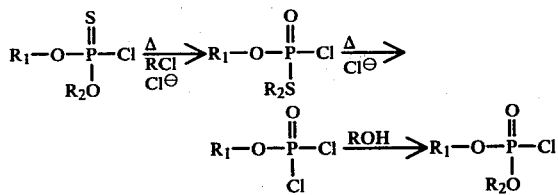

where $R_1$ and $R_2$ can be the same or different $C_{1-8}$ alkyl groups, the temperature ranges from 100°–150° C. and the necessary contact with ionic species is provided for a time sufficient to facilitate the degradation reaction.

In a related disclosure with a similar purpose, U.S. Pat. No. 3,089,890 teaches treating a distilled crude phosphorochloridothioate with water, separating the organic phase and drying to upgrade the crude and recover substantially contaminant-free phosphorochloridothioate. Most recently, U.S. Pat. No. 4,159,289 teaches a process for removal of sulfur impurities from phosphorochloridothioates by distillation in the presence of a naphthalenic liquid hydrocarbon sulfur solubilizing or suspending agent. However, such distillation would not remove the oxygenated phosphorus impurities made during production of phosphorochloridothioates or from their thermal degradation products. Thus, the need for maintaining and improving the quality of phosphorochloridothioates is readily apparent and required in subsequent processes employing same and in products derived therefrom.

THE INVENTION

It has now been found that the separation of certain impurities from dialkyl phosphorochloridothioates can be made simply, without additional capital cost and with very small operational costs, by the addition to the crude dialkyl phosphorochloridothioate of a suitable treating agent. More specifically, this invention includes a process for purifying $C_{1-8}$ dialkyl phosphorochloridothioate compounds comprising treating a crude mixture of said $C_{1-8}$ dialkyl phosphorochloridothioate and a corresponding $C_{1-8}$ dialkyl phosphate impurity associated therewith with an alcohol so that said impurity and said alcohol form a reaction product having sufficiently different physical properties to permit separation from said $C_{1-8}$ dialkyl phosphorochloridothioate and separating said $C_{1-8}$ dialkyl phosphorochloridothioate from the resulting mixture. In a particularly preferred aspect of this invention there is provided a process for the continuous separation of $C_{1-8}$ dialkyl phosphate impurities from a $C_{1-8}$ dialkyl phosphorochloridothioate compound in admixture therewith comprising adding an alcohol to said mixture and distilling said mixture whereby said $C_{1-8}$ dialkyl phosphorochloridothioate is separated from the $C_{1-8}$ dialkyl phosphate-alcohol reaction product which remains with the distillation residue.

The crude dialkyl phosphorochloridothioate useful in the purification process of this invention can be produced by a number of the prior art methods taught in the above-mentioned references and the teachings of those references, specifically, U.S. Pat. Nos. 3,089,890; 3,502,750; 3,836,610; 3,897,523; 4,025,586; and 4,159,289; are hereby incorporated by reference as if fully set forth. The prior art methods for producing dialkyl phosphorochloridothioates are useful for their teachings until the steps of purification or separation of the product from the reaction mixture or solvent are discussed. The advantage of the process of this invention is that a product having lower amounts of impurities is provided without large expenditures for capital equipment or processing costs. Typically, the crude dialkyl phosphorochloridothioate can have up to 3 percent by weight of oxygenated phosphorus compounds, for example, diethyl chlorophosphate. Additionally, after formation, exposure of the product dialkyl phosphorochloridothioate to heat causes degradation and increases the content of oxygenated phosphorus compound impurities such as dialkyl chlorophosphates. For instance, distillation of diethyl phosphorochloridothioate can increase the amount of diethyl phosphoryl chloride (i.e., diethyl chlorophosphate). However, when separation or purification takes place in the presence of an alcohol, there is a marked decrease in the amount of such oxygenated phosphorus compound impurities which accompany the dialkyl phosphorochloridothioate. Without being limited to any form or mode of action or theoretical mechanism of the invention, it is believed that the alcohol reacts with the oxygenated phosphorus impurities selectively, altering their physical properties and allowing separation from the product dialkyl phosphorochloridothioates by means of conventional techniques.

The alcohol useful in this invention is one which when reacted with oxygenated phosphorus compound impurities produced in a process for preparing dialkyl phosphorochloridothioates will so alter the physical and chemical properties of the impurity by producing a reaction product that conventional techniques can be used to separate the reaction product from the dialkyl phosphorochloridothioate. Generally, a suitable alcohol can have from 2 to 30 or more carbon atoms and can be a straight or branched chain alcohol or mixtures of straight chain alcohols, branched chain alcohols or both. Further, the alcohols useful in the process of this invention contain at least one hydroxyl group and can have 1, 2 3, or 4 hydroxyl groups. Preferably, suitable alcohols have a sufficient number of carbon atoms so that the reaction product of the alcohol and the oxygenated phosphorus compound impurity will have a significantly higher boiling point or lower vapor pressure then the desired dialkyl phosphorochloridothioates, allowing easy separation by distillation. Preferably, a suitable alcohol will produce a reaction product having a boiling point greater than about 100° C. at pressures of 15 mm Hg.

Typical of alcohols which are suitable for use in the process of this invention are 1-hexanol, 1-octanol, 1-nonanol, 1-decanol, 1-undecanol, ethyl alcohol, 1-dodecanol, tridecanol, 1-tetradecanol, 1-hexadecanol, 1-heptadecanol, 1-octadecanol, glycidol and the like. Also useful are 1,5-pentanediol, 1,3-propanediol, 1,2-propanediol, 1,6-hexanediol, 1,4-tetradecanediol, pentaerythritol, diethylene glycol, triethylene glycol, glyceryl monostearate, 2-ethyl-2-(hydroxymethyl)-1,2-propanediol. Also, various commercially available mixtures of alcohols containing 6/8/10 carbon chain lengths in weight ratios of 1:2:2, respectively; mixtures of 70–80% 1-decanol and 20–30% dodecanol; mixtures of 1-tetradecanol and 1-hexadecanol in weight ratios of about 2:1, respectively, and the like. A particularly cost effective alcohol is a mixture of fatty alcohols and paraffins in a weight ratio of 70:30, respectively, of chain length greater than twenty carbon atoms but not more than about 30 carbon atoms and having a boiling point of 350° C. and a melting point of about 45° C., both at atmospheric pressure.

The alcohols described above are useful in treating the dialkyl phosphorochloridothioate in amounts sufficient for good reaction with the oxygenated phosphorus compound impurities so that such impurities represent not more than about 0.5% of the product composition by weight. The amount of a particular alcohol required will vary depending on the number of hydroxyl groups contained. Thus, for a given amount of a monohydroxy compound, only one-half that amount of a dihydroxy compound will be required, generally speaking. In terms of the product dialkyl phosphorochloridothioate, the amount of alcohol can range, in general, from about 0.05 to about 0.5 pounds of alcohol per pound of dialkyl phosphorochloridothioate. Although a definite range has been expressed, it should be noted that the lower limit is only that amount required to react with substantially all of the oxygenated phosphorus compound impurities while the upper limit is defined by practical considerations of the separation technique employed, cost of alcohol reagent, equipment size and alcohol regeneration and recycle. A more preferred range of alcohol treatment level is from about 0.1 to about 0.3 pounds of alcohol per pound of dialkyl phosphorochloridothioate.

The treatment of crude dialkyl phosphorochloridothioates with alcohol is generally effective in reasonably short times at somewhat elevated temperatures. However, the time and temperature relationship can be adjusted to produce effective impurity removal at low temperatures and relatively longer contact periods or conversely at higher temperatures in relatively shorter contact periods. In general, treatment with alcohols occurs at 100° C. up to temperatures at which the dialkyl phosphorochloridothioate is severely thermally degraded. Such higher temperatures should also be avoided to prevent the danger of explosive decomposition. Generally, temperatures from 100° C. to about 130° C., depending upon the particular alkyl groups in the product dialkyl phosphorochloridothioate, can be used. When the product has lower alkyl groups, it should be kept nearer the lower end of the temperature range; while products having longer chain alkyl groups can withstand temperatures nearer the high end of the temperature range. Contact periods from a few minutes to about one hour or more are typical, depending upon the alcohol, the separation system, the temperature, etc. It is only necessary to select these parameters and follow the reaction by sampling over time to establish the point at which substantially all of the impurities have disappeared in order to establish a practical treatment procedure.

The prior art contains adequate teaching for separating product dialkyl phosphorochloridothioate from sulfur, reaction mixture, solvent, etc. Such techniques are useful for separating the reaction product of the alcohol and impurities also. Thus, after treatment with a suitable alcohol the resultant dialkyl phosphorochloridothioate reaction mixture can be heated to distill off the desired dialkyl phosphorochloridothioate. Such distillation can be carried out as flash distillation, vacuum distillation, steam distillation, wiped-film distillation or other conventional distillation operations. In U.S. Pat. No. 4,159,289, there is described an improved process for preparation of dialkyl phosphorochloridothioates in which distillation is carried out in the presence of a sulfur solubilizing agent or suspending agent. In a preferred aspect of this process after treatment with alcohol, the resultant mixture of alcohol and crude dialkyl phosphorochloridothioate containing oxygenated phosphorus impurities is fed to a distillation section of conventional design and the dialkyl phosphorochloridothioate is taken overhead as a product substantially free of oxygenated phosphorus compound impurities and the reaction product of such impurities with the alcohol remains with the bottoms product. The advantage of this purification process is that no further treatment of the product is required. The distillation section can be designed and operated in a manner such that substantially low losses of product dialkyl phosphorochloridothioate are incurred and practically complete elimination of oxygenated phosphorus compounds is achieved.

As a further illustration describing the process of this invention, the following non-limiting examples are provided. The examples are to be considered only as illustrative of the process of this invention. All percentages are by weight unless otherwise noted.

EXAMPLE 1

This example demonstrates the use of dodecanol and a mixture of $C_{20+}$ alcohols and paraffins as a treatment for oxygenated phosphorus impurities in diethyl phosphorochloridothioate.

An 8-inch long Vigreux column was set up for flash distillation at 72 mm Hg pressure over a one hour period. Bottoms temperature at these conditions was 130°–135° C. and the overhead temperature was 120° C. The feed material was the same in each instance except as noted below. Three runs were made with Run (1) having no alcohol added to the feed, Run (2) having dodecanol added, and Run (3) having a "$C_{20+}$ alcohol mixture" added. As used herein, the term "$C_{20+}$ alcohol mixture" refers to a mixture of approximately 70 weight percent alcohols having a chain length of 20 carbon atoms or greater and 30 weight percent paraffins of about the same carbon chain lengths as the alcohols which mixture has a 45° C. melting point, a boiling point of greater than 200° C. at 5 mm Hg and a molecular weight of 361. The amounts and analysis of the product and remaining oxygenated phosphorus compounds are given in the following table.

TABLE I

| | Flash Distillation of Diethyl Phosphorochloridothioate in the Presence of Alcohol | | | |
|---|---|---|---|---|
| | Total Weight | DECTP[a] | TETP[b] | DECP[c] |
| Run 1 - Control (No Alcohol) | | | | |
| Feed (g) | 235.1 | 151.9 | 1.7 | 0.09 |
| Distillate (g) | 82.4 | 78 | 0.3 | 0.31 |

TABLE I-continued

Flash Distillation of Diethyl Phosphorochloridothioate in the Presence of Alcohol

|  | Total Weight | DECTP[a] | TETP[b] | DECP[c] |
|---|---|---|---|---|
| Bottoms (g) | 149.9 | 62.5 | 0.52 | 0.57 |
| Percent Accounted for (%) | 98.8 | 93.1 | 48 | — |
| Run 2 - 4.6 Wt % Dodecanol in Feed | | | | |
| Feed (g) | 206.2[d] | 127.1 | 1.4 | 0.08 |
| Distillate (g) | 61.1 | 58.4 | 0.24 | 0 |
| Bottoms (g) | 143.1 | 61.8 | 0.67 | 0 |
| Percent Accounted for (%) | 99.0 | 94.6 | 65 | — |
| Run 3 - 6.3 Wt % $C_{20+}$ Alcohol in Feed | | | | |
| Feed (g) | 219.3[e] | 132.8 | 1.5 | 0.09 |
| Distillate (g) | 55.5 | 53.1 | 0.2 | 0.02 |
| Bottoms | 162.1 | 72.7 | 0.7 | 0.06 |
| Percent Accounted for (%) | 99.2 | 94.7 | 60 | — |

[a]DECTP is diethyl chlorothiophosphate (i.e., diethyl phosphorochloridothioate)
[b]TETP is triethylthiophosphate
[c]DECP is diethylchlorophosphate
[d]Feed contains 196.7 g of DECTP plus 9.5 g dodecanol
[e]Feed contains 205.5 g DECTP plus 13.8 g of $C_{20+}$ alcohol As can be seen from Run 1, the amounts of DECP impurity greatly increases in the distillate and bottoms during distillation. However, the use of dodecanol or $C_{20+}$ alcohol mixture prevented the increase of DECP in the distillate compared with Run 1.

EXAMPLE 2

This example demonstrates the treatment of diethyl phosphorochloridothioate with various alcohols at the same relative level of hydroxyl group concentration by heating at 125° C. and analyzing samples over time. The types of alcohol, amounts and results are given in the following table. In the table, the following designations are used for convenience: "OH%" means the weight percentage of hydroxyl groups in the particular alcohol; "Wt %" is based on the weight of diethyl phosphorochloridothioate; "OH Added" is the product of "OH%" and "Wt %" columns expressed as a percentage to indicate the actual weight percentage of hydroxyl groups added based on weight of diethyl phosphorochloridothioate; "OH/DECP Added M. Ratio" is the molar ratio of hydroxyl groups to diethyl chlorophosphate groups in the system initially and is calculated from the weight percent of OH groups added and the initial concentration of diethyl chlorophosphate, "DECP/DECTP at Hour" is the ratio of impurity diethyl chlorophosphate to product diethyl chlorothiophosphonate (i.e., diethyl phosphorochloridothioate) initially and as analyzed by vapor phase chromatography after 1, 2, 3 and 4 hours with all initial readings being 0.66.

TABLE II

Alcohol Reaction with DECP[a] at 125° C.

| Alcohol Compound | Amount of Alcohol Added OH % | Wt % | OH Added Wt % | OH/DECP[a] Added M Ratio | DECP/DECTP[b] at Hour 0 | 1 | 2 | 3 | 4 |
|---|---|---|---|---|---|---|---|---|---|
| Dodecanol | 9.1 | 7.7 | 0.7 | 10.8 | .66 | — | .30 | .16 | — |
|  | 9.1 | 7.0 | 0.64 | 9.9 | — | .45 | .26 | .13 | — |
| Diethylene Glycol | 32 | 2.0 | 0.64 | 9.9 | — | .41 | .32 | — | — |
|  | 32 | 2.0 | 0.64 | 9.9 | — | .43 | .28 | .17 | — |
| Triethylene Glycol | 23 | 2.0 | 0.46 | 7.0 | — | .56 | — | — | — |
|  | 23 | 2.8 | 0.63 | 9.8 | — | .56 | .43 | .25 | .26 |
| $C_{20+}$ Alcohols | 3 | 21.2 | 0.63 | 9.8 | — | .52 | .33 | .18 | .08 |
| 2-Ethyl-2-(Hydroxymethyl)-1,2-propane Diol | 38 | 1.7 | 0.64 | 9.9 | — | .52 | .25 | .18 | — |
|  |  |  |  |  | — | .54 | .26 | .12 | .13 |
| Pentaerythritol | 49.9 | 1.3 | 0.64 | 9.9 | — | .64 | — | .38 | .23 |
| 1,3-Propane Diol | 44.7 | 1.43 | 0.64 | 9.9 | — | .33 | .17 | .05 | .10 |
| 1,4-Butane Diol | 37.7 | 1.7 | 0.64 | 9.9 | — | .17 | .05 | .12 | .26 |
| 1,6-Hexane Diol | 28.8 | 2.2 | 0.64 | 9.9 | — | .26 | .24 | — | .42 |
| 1,5-Pentane Diol | 32.6 | 1.95 | 0.64 | 9.9 | — | .20 | .13 | .16 | .31 |
| Glyceryl Monostearate | 9.48 | 6.7 | 0.64 | 9.9 | — | .41 | .25 | .07 | .00 |

[a]DECP is diethyl chlorophosphate
[b]DECTP is diethyl chlorothiophosphonate

From the foregoing Example 2, it can be seen that when equivalent amounts of hydroxyl groups are used, all of the alcohols tested reacted with the oxygenated phosphorus compound impurities and significantly reduced their concentration during the first two hours at the indicated temperature. However, thermal degradation occurring after 3 hours in some cases increased DECP concentrations and more alcohol would have to be added to accommodate the increased impurity levels.

EXAMPLE 3

This example illustrates the use of a continuous distillation column to separate product dialkyl phosphorochloridothioate from oxygenated phosphorus compound impurities after treatment with alcohol.

A 4-inch pyrex pipe packed column having about 8 theoretical separation stages and a feed point at about the mid point of the column above the reboiler was set up to operate at an overhead condenser pressure of 15 mm Hg and an overhead temperature of about 84° C. The pressure below the bottom of the packing was 21 mm Hg and the sump temperature was about 132° C. as produced by 50–70 psig of steam. The feed was typically 6.3 pounds per hour of crude diethyl phosphorochloridothioate from which all lower boiling materials had been removed. A typically expected feed to the column taken from column material balance follows:

| Component | Weight % |
|---|---|
| DECTP | 59.23 |
| DECP | 0.19 |
| TETP | 0.13 |
| Sulfur Solubilizing Agent | 12.95 |
| Other Phosphorus Compounds | 13.77 |
| Sulfur | 4.4 |
| Antifouling Agent | 0.89 |
| $C_{20+}$ Alcohol Mixture | 8.44 |
| | 100.00 |

The above feed composition was calculated after some experience in column operation determined the necessary feed amounts of alcohol. Prior to the addition of alcohol, the distillation of crude feed streams, similar to the composition given above but without the antifouling agent and alcohol, were run under the given column conditions. The average amounts of oxygenated phosphorus impurity, specifically DECP, during the course of the runs was from 1–3 weight percent. Addition of alcohol to the column feed reduced the overhead distillate amount of DECP to from 0.1 to 0.4 weight percent. Usually, the alcohol was added to the crude feed prior to the feed entering the distillation section. After low-boiling materials were removed, analysis of samples of product column feed allowed calculation of material balances which indicated the above typical feed composition. The following table summarizes the distillation operations and results. In the table, the "Feed" heading refers to the crude product yield of diethyl phosphorochloridothioate as produced and before purification, the "Total Time of Column Operation" refers to the number of hours that the distillation section operated, and "Contact Time" refers to both the "Total" time that the alcohol was in contact with the crude diethyl phosphorochloridothioate and includes "In Col." time which is the actual residence or hold-up time in the product distillation column.

TABLE III

| | Continuous Distillation of Diethyl | | | | | |
|---|---|---|---|---|---|---|
| Run No. | Feed (Avg. % Yield of DECTP Reaction Process) | $C_{20}$ Alcohol Added (Wt % Based on DECTP in Feed) | Total Time of Column Operation (hrs.) | Contact Time | | Avg. Concentration of DECP in Product (Wt %) |
| | | | | Total (min.) | In Col. (min.) | |
| 4-1 | 89.2 | 0 | 30 | 0 | 0 | 0.7 |
| 4-2 | 79.9 | 0 | 111.9 | 0 | 0 | 0.2→1.0 |
| 4-3 | 78.1 | 0 | 42.0 | 0 | 0 | 3.0 |
| 4-4 | 90.65 | 0 | 74.0 | 0 | 0 | 2.0→3 |
| —4A* | 90.65 | 20 | 74.0 | 95 | 45 | 0.4 |
| 4-5 | 85.96 | 22 | 125 | 95 | 45 | 0.2 |
| 4-6 | 80.93 | 20** | 54.5 | 95 | 45 | 1.0→0.1 |
| 4-7 | 78.4 | 25 | 212 | 189 | 45 | 0.3→1.3 |
| 4-8 | 88.8 | (12.5) | 240 | 100 | | 0.1→0.2 |
| | 84.97 | (9.7) 245 | 240 | 100 | | 0.1→0.4 |
| | 85.5 | (6.7) | 250 | 105 | | 1.0 |

*Alcohol used during a portion of Run 4
**Alcohol treatment began after 8 hours of operation From the foregoing, it can be clearly seen that addition of 6.7 to 25 weight percent of a $C_{20+}$ alcohol mixture effectively reduces the oxygenated phosphorus compounds in the product distillate. Using the treatment process of this invention, purified diethyl phosphorochloridothioate of >99 weight percent assay can be easily produced on a regular basis.

Having described the process of this invention, one skilled in the art can readily envision various changes within the scope and spirit of the process of the invention. It is therefore desired to limit the invention only by the lawful scope of the following claims.

What is claimed is:

1. A process for purifying $C_{1-8}$ dialkyl phosphorochloridothioate compounds comprising treating a crude mixture of said $C_{1-8}$ dialkyl phosphorochloridothioate and a corresponding $C_{1-8}$ dialkyl phosphate impurity associated therewith with an alcohol so that said impurity and said alcohol form a reaction product having sufficiently different physical properties to permit distillation of said $C_{1-8}$ dialkyl phosphorochloridothioate and distilling said $C_{1-8}$ dialkyl phosphorochloridothioate from the resulting mixture.

2. The process of claim 1 in which said $C_{1-8}$ dialkyl phosphorochloridothioate compound is selected from dimethyl and diethyl phosphorochloridothioates.

3. The process of claim 1 in which said dialkyl phosphate impurity is a diethyl or dimethyl phosphate impurity.

4. The process of claim 1 in which said dialkyl phosphate impurity is a diethyl phosphate impurity.

5. The process of claim 1 in which said dialkyl phosphate impurity is diethyl chlorophosphate.

6. The process of claim 1 in which said alcohol is a compound having from 2–30 carbon atoms and being composed of carbon and hydrogen except for hydroxyl groups.

7. The process of claim 1 in which said alcohol has 1, 2, 3 or 4 hydroxyl groups.

8. The process of claim 1 in which said alcohol has from 10–30 carbon atoms and is composed solely of carbon and hydrogen atoms except for hydroxyl groups.

9. The process of claim 1 in which said alcohol is a mixture of alcohols having from 20–30 carbon atoms and is composed solely of carbon and hydrogen atoms except for the hydroxyl groups.

10. The process of claim 1 in which said alcohol is a mixture of alcohols having from 20–30 carbon atoms and is composed solely of carbon and hydrogen atoms except for the hydroxyl groups.

11. A process for the continuous distillation of $C_{1-8}$ dialkyl phosphate impurities from a $C_{1-8}$ dialkyl phosphorochloridothioate compound in admixture therewith comprising adding to said mixture an alcohol and distilling said mixture whereby said $C_{1-8}$ dialkyl phosphorochloridothioate is distilled from the $C_{1-8}$ dialkyl phosphate-alcohol reaction product which remains with the distillation residue.

12. The process of claim 11 in which said $C_{1-8}$ dialkyl phosphorochloridothioate compound is selected from dimethyl and diethyl phosphorochloridothioates.

13. The process of claim 11 in which said dialkyl phosphate impurity is a diethyl or dimethyl phosphate impurity.

14. The process of claim 11 in which said dialkyl phosphate impurity is a diethyl phosphate impurity.

15. The process of claim 11 in which said dialkyl phosphate impurity is diethyl chlorophosphate.

16. The process of claim 11 in which said alcohol is a compound having from 2–30 carbon atoms and being composed of carbon and hydrogen except for hydroxyl groups.

17. The process of claim 11 in which said alcohol has 1, 2, 3 or 4 hydroxyl groups.

18. The process of claim 11 in which said alcohol has from 10–30 carbon atoms and is composed solely of carbon and hydrogen atoms except for hydroxyl groups.

* * * * *

UNITED STATES PATENT AND TRADEMARK OFFICE
CERTIFICATE OF CORRECTION

PATENT NO. : 4,247,490

DATED : January 27, 1981

INVENTOR(S) : Charles R. Bergeron, et al

It is certified that error appears in the above—identified patent and that said Letters Patent are hereby corrected as shown below:

Column 7, in Table I, "Alcohol in Feed" should be transferred to the line above, after "$C_{20+}$" and should be underscored.

Column 8, in Table II, the heading "OH Added" should be underscored and the heading "OH/DECP$^a$ Added" should be underscored.

Column 10, line 65, reads "claim 1", should read -- claim 11 --.

Signed and Sealed this

Twenty-eighth Day of April 1981

[SEAL]

Attest:

RENE D. TEGTMEYER

*Attesting Officer*     *Acting Commissioner of Patents and Trademarks*